United States Patent
Fukuda (10) Patent No.: US 9,603,664 B2
(45) Date of Patent: Mar. 28, 2017

(54) ABLATION CATHETER SYSTEM

(71) Applicant: OLYMPUS CORPORATION, Tokyo (JP)

(72) Inventor: Hiroshi Fukuda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 319 days.

(21) Appl. No.: 13/867,348

(22) Filed: Apr. 22, 2013

(65) Prior Publication Data
US 2013/0317491 A1 Nov. 28, 2013

(30) Foreign Application Priority Data
May 23, 2012 (JP) ................................ 2012-117737

(51) Int. Cl.
*A61B 18/24* (2006.01)
*A61B 18/14* (2006.01)
*A61B 18/00* (2006.01)

(52) U.S. Cl.
CPC .......... *A61B 18/24* (2013.01); *A61B 18/1492* (2013.01); *A61B 2018/00029* (2013.01); *A61B 2018/00035* (2013.01); *A61B 2018/00351* (2013.01); *A61B 2018/00357* (2013.01); *A61B 2018/00363* (2013.01); *A61B 2018/00577* (2013.01); *A61B 2018/00595* (2013.01);
(Continued)

(58) Field of Classification Search
CPC .... A61B 2018/00994; A61B 2218/002; A61B 2218/007; A61B 2218/00029; A61B 18/12; A61B 18/22; A61B 18/24
USPC ..................................... 606/2–19; 607/88–89
See application file for complete search history.

(56) References Cited

U.S. PATENT DOCUMENTS 5,401,272 A * 3/1995 Perkins .............. A61B 18/1442
606/15
5,683,366 A * 11/1997 Eggers ................... A61B 18/12
604/114
(Continued)

FOREIGN PATENT DOCUMENTS

JP S63-500987 A 4/1988
JP H06-205789 A 7/1994
(Continued)

OTHER PUBLICATIONS von der Linde, The Physical Mechanisms of Short-Pulse Laser Ablation, 2000, Applied Surface Science, 154-155 (2000) 1-10.*
(Continued)

*Primary Examiner* — Lynsey Crandall
*Assistant Examiner* — Qingjun Kong
(74) *Attorney, Agent, or Firm* — Scully, Scott, Murphy & Presser, PC (57) ABSTRACT

In order to sufficiently cauterize a target site existing in a deep portion of a cardiac muscle tissue even in the case where the fat layer attached to an epicardium is thick or where the cardiac muscle is thickened due to cardiac hypertrophy and the like, provided is an ablation catheter comprising: an elongated catheter main body; an electrode for ablation placed in a leading end part of the catheter main body; and an optical fiber that is placed along a longitudinal direction of the catheter main body, includes an emission end formed on a leading end surface of the catheter main body, and emits a laser beam guided therethrough from the emission end.

5 Claims, 8 Drawing Sheets

(52) U.S. Cl.
CPC ............ *A61B 2018/00625* (2013.01); *A61B 2018/00642* (2013.01); *A61B 2018/00839* (2013.01); *A61B 2018/00994* (2013.01); *A61B 2218/002* (2013.01); *A61B 2218/007* (2013.01)

(56) References Cited

U.S. PATENT DOCUMENTS

| 5,840,025 | A  | * | 11/1998 | Ben-Haim ............ A61B 34/20 600/424 |
| 5,871,523 | A  | * | 2/1999  | Fleischman ............ A61N 1/403 606/33 |
| 6,085,115 | A  | * | 7/2000  | Weaver et al. ................ 600/509 |
| 6,522,930 | B1 | * | 2/2003  | Schaer et al. ................. 607/101 |
| 7,879,011 | B2 | * | 2/2011  | Chang ............... A61M 25/0084 604/164.13 |
| 2007/0287998 | A1 | | 12/2007 | Sharareh et al. |
| 2012/0330293 | A1 | | 12/2012 | Arai et al. |

FOREIGN PATENT DOCUMENTS

| JP | H10-033549 A | 2/1998 |
| JP | H10-290805 A | 11/1998 |
| JP | 4040672 B | 1/2008 |
| JP | 2009-148550 A | 7/2009 |
| WO | 87/01273 A1 | 3/1987 |
| WO | 2011/105631 A1 | 9/2011 |
| WO | WO 2011155424 A1 * | 12/2011 |

OTHER PUBLICATIONS

Machine translation for Catheter for Measuring Electric Potential by Harada et al (WO 2011155424 A1).*
Wagshall et al, A Novel Catheter Design for Laser Photocoagulation of the Myocardium to Ablate Ventricular Tachycardia, J. Interventional Cardiac Electrophysiology, Jul. 13-22, 2002.*
English Abstract of WO 9502995 A1 dated Feb. 2, 1995.

* cited by examiner

ABLATION CATHETER SYSTEM

BACKGROUND OF THE INVENTION

1. Field of the Invention

The present invention relates to an ablation catheter.

2. Description of Related Art

In an ablation catheter that has been known up to now, an electrode provided in the catheter leading end is brought into contact with an epicardium, and a high-frequency current is thus fed thereto, whereby a cardiac muscle tissue is cauterized (see, for example, the Publication of Japanese Patent No. 4040672 (hereinafter referred to as "JP 4040672")).

Unfortunately, according to the ablation catheter disclosed in JP 4040672, in the case where the fat layer attached to the epicardium is thick or where the cardiac muscle is thickened due to cardiac hypertrophy and the like, the electrode in the catheter leading end cannot be brought close to a target site existing in a deep portion of the cardiac muscle tissue, and hence sufficient cauterization cannot be performed.

The present invention, which has been made in view of the above-mentioned circumstances, has an object to provide an ablation catheter capable of sufficiently cauterizing a target site existing in a deep portion of a cardiac muscle tissue even in the case where the fat layer attached to an epicardium is thick or where the cardiac muscle is thickened due to cardiac hypertrophy and the like.

BRIEF SUMMARY OF THE INVENTION

In order to achieve the above-mentioned object, the present invention provides the following solutions.

An aspect of the present invention provides an ablation catheter comprising: an elongated catheter main body; an electrode for ablation placed in a leading end part of the catheter main body; and an optical fiber that is placed along a longitudinal direction of the catheter main body, includes an emission end formed on a leading end surface of the catheter main body, and emits a laser beam guided therethrough from the emission end.

The ablation catheter according to the aspect may further comprise a washing liquid supply channel that is placed along the longitudinal direction of the catheter main body and is opened on the leading end surface of the catheter main body.

The ablation catheter according to the aspect may further comprise a baffle that is placed in front of the opening of the washing liquid supply channel and dams at least part of supplied washing liquid to cause the part to flow in a direction along the leading end surface of the catheter main body.

The ablation catheter according to the aspect may further comprise a cooling liquid supply channel that is placed along the longitudinal direction of the catheter main body and causes cooling liquid to circulate in the vicinity of the electrode for ablation.

According to the aspect, part of the electrode for ablation placed in the leading end part of the catheter main body may be divided so as to be usable as an electrode for biopotential measurement.

DETAILED DESCRIPTION OF THE INVENTION

An ablation catheter 1 according to a first embodiment of the present invention is described below with reference to the drawings.

Figure 1:
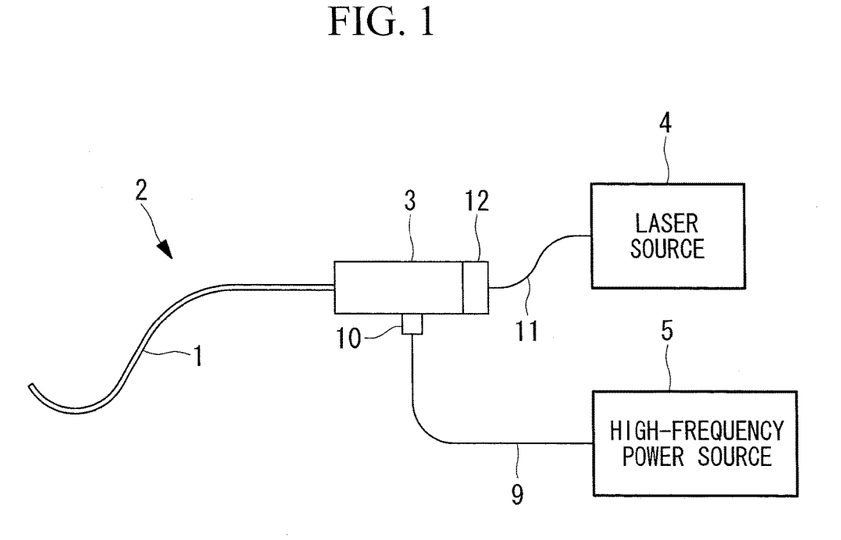
FIG. 1 is a diagram illustrating an ablation system to which an ablation catheter according to a first embodiment of the present invention is attached.

An ablation catheter 1 according to the present embodiment is used for an ablation system 2 illustrated in FIG. 1.

The ablation system 2 of FIG. 1 includes: the ablation catheter 1 according to the present embodiment; a grip unit 3 that is connected to the base end side of the ablation catheter 1 and is gripped by an operator; a laser source 4 connected to the grip unit 3; and a high-frequency power source 5 connected to the grip unit 3.

Figure 2:
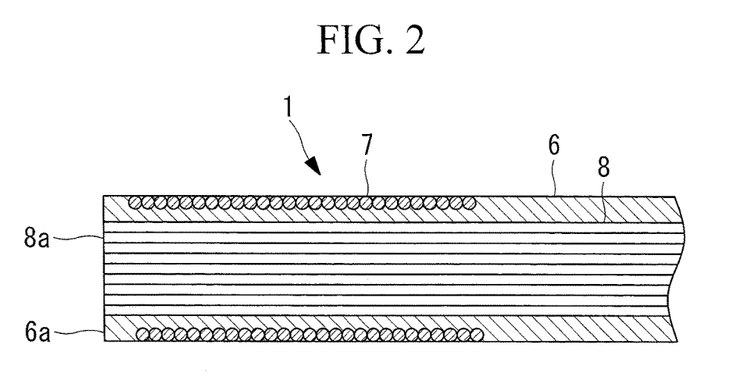
FIG. 2 is a longitudinal sectional view for describing a structure of a leading end part of the ablation catheter according to the present embodiment, the ablation catheter being used for the system of FIG. 1.

As illustrated in FIG. 2, the ablation catheter 1 includes: an electrode (electrode for ablation) 7 configured by winding a wire around a leading end part of an elongated catheter main body 6; and optical fibers 8 that are placed along the longitudinal direction of the catheter main body 6 and each includes an emission end 8a formed on a leading end surface 6a of the catheter main body 6.

To the grip unit 3, a cable 9 extending from the high-frequency power source 5 is connected by an electrical connector 10, and an optical cable 11 extending from the laser source 4 is connected by an optical connector 12.

Further, in the grip unit 3, the electrode 7 is connected to the cable 9 extending from the high-frequency power source 5 by a wiring line (not illustrated) connected to the electrical connector 10. Furthermore, in the grip unit 3, base ends of the optical fibers 8 are connected to the optical cable 11 extending from the laser source 4 by the optical connector 12.

Examples of the used laser source 4 include a short pulsed laser source that generates a pulsed laser beam having high peak energy and a wavelength with a large attenuation coefficient in tissue. It is preferable that the pulsed laser beam have a pulse width of 500 μsec or less. In particular, an excimer laser and a Q-switch solid-state laser are preferably used. It is preferable that the laser beam have a wavelength with a large attenuation coefficient in tissue, for example, 300 to 450 nm.

An operation of the ablation catheter 1 thus configured according to the present embodiment is described below.

A target site existing in a deep portion of a cardiac muscle tissue is cauterized in the following manner using the ablation catheter 1 according to the present embodiment. First, the leading end part of the ablation catheter 1 is inserted from the outside of a body into a pericardium through a sheath inserted from below a xiphoid process into the pericardium. With the use of an endoscope similarly inserted from below the xiphoid process into the pericardium, it is checked whether or not the leading end of the ablation catheter 1 is opposed to the target cardiac muscle tissue or adipose tissue. Then, a pulsed laser beam is oscillated from the laser source 4.

The pulsed laser beam oscillated from the laser source 4 passes through the optical cable 11 and the optical connector 12, enters the base end parts of the optical fibers 8 provided in the ablation catheter 1, is guided inside of the catheter main body 6, and is emitted from the emission ends 8a formed on the leading end surface 6a of the catheter main body 6. Consequently, when the pulsed laser beam is applied to the cardiac muscle tissue or the adipose tissue, the cardiac muscle tissue or the adipose tissue is evaporated by the high peak energy of the pulsed laser beam to be locally removed.

In this way, the cardiac muscle tissue or the adipose tissue is removed while the leading end part of the catheter main body 6 is further inserted into the removed portion, whereby the leading end part of the catheter main body 6 can be brought close to the target site existing in the deep portion of the cardiac muscle tissue.

In this state, the oscillation of the pulsed laser beam from the laser source 4 is stopped, and feeding of a high-frequency current from the high-frequency power source 5 is started.

The high-frequency voltage signal supplied from the high-frequency power source 5 passes through the cable 9, the electrical connector 10, and the wiring line (not illustrated) inside of the catheter main body 6, is supplied to the electrode 7 placed in the leading end part of the catheter main body 6, and cauterizes the cardiac muscle tissue close to a portion around the electrode 7.

In this way, with the ablation catheter 1 according to the present embodiment, the cardiac muscle tissue or the adipose tissue is evaporated by the pulsed laser beam having high peak energy, whereby the leading end part of the catheter main body 6 can be brought close to the target site existing in the deep portion of the cardiac muscle tissue. As a result, even in the case where the adipose tissue attached to an epicardium is thick or where the cardiac muscle tissue is thickened due to cardiac hypertrophy and the like, the electrode 7 can be brought close to the target site existing in the deep portion of the cardiac muscle tissue, and the target site can be sufficiently cauterized, which is advantageous.

That is, the elongated catheter main body 6 is introduced to the fat layer attached to the epicardium, and a laser beam is emitted from the emission ends of the optical fibers 8 in the state where the leading end surface of the catheter main body 6 is opposed to the fat layer.

Consequently, the adipose tissue or the cardiac muscle tissue can be removed without carbonization of the tissue, so that the leading end part of the catheter main body 6 can reach the target site existing in the deep portion of the cardiac muscle tissue. Then, in this state, the target site can be sufficiently cauterized by the electrode for ablation from a position close to the target site.

Accordingly, the present embodiment produces an effect of sufficiently cauterizing the target site existing in the deep portion of the cardiac muscle tissue even in the case where the fat layer attached to the epicardium is thick or where the cardiac muscle is thickened due to cardiac hypertrophy and the like.

Next, an ablation catheter 20 according to a second embodiment of the present invention is described below with reference to the drawings.

In the following description of the present embodiment, elements having the same configurations as those in the ablation catheter 1 according to the first embodiment described above are denoted by the same reference signs, and description thereof is omitted.

Figure 4:
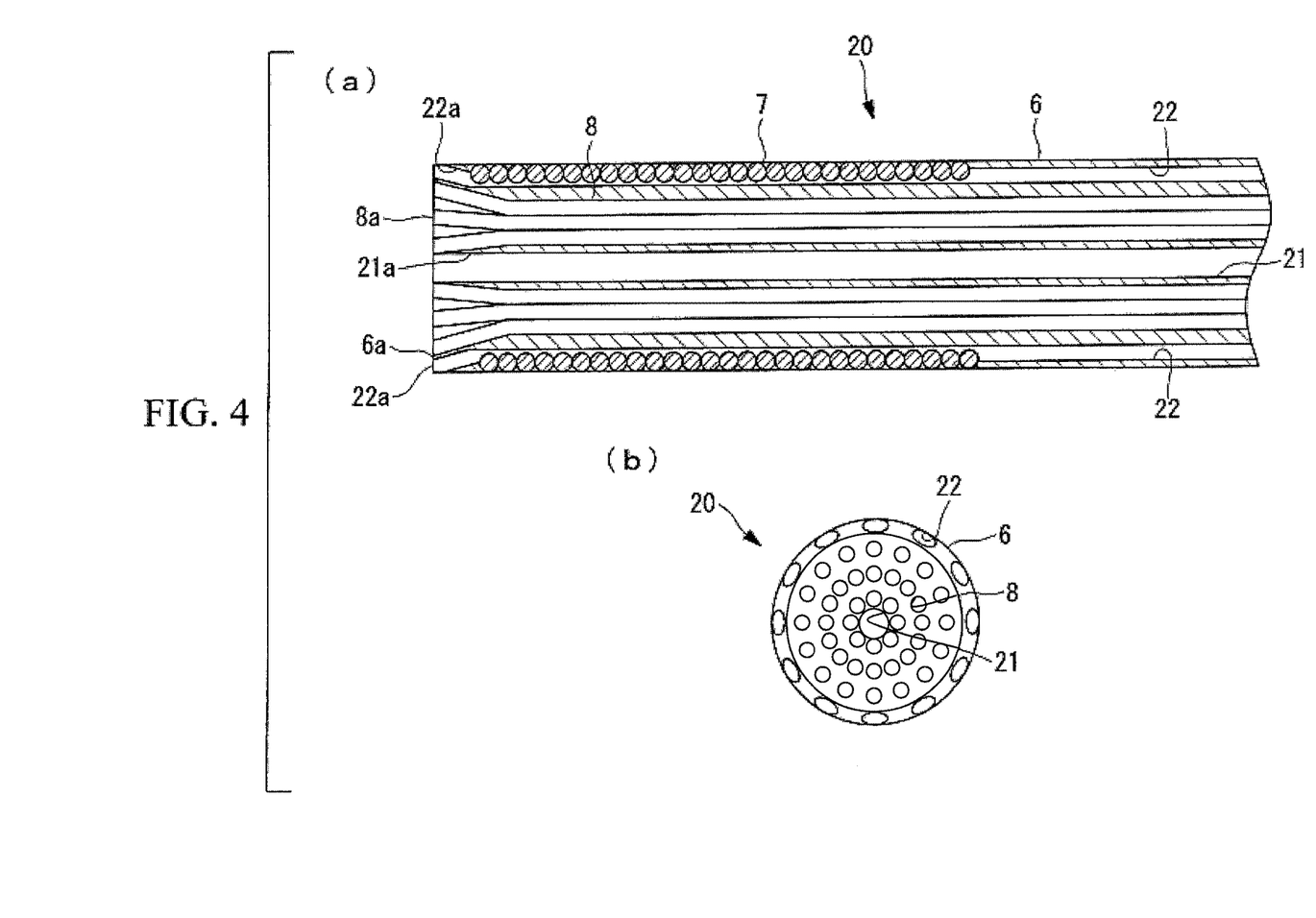
FIGS. 4(A) and 4(B) are respectively a longitudinal sectional view and a front view for describing a structure of a leading end part of the ablation catheter according to the present embodiment, the ablation catheter being used for the system of FIG. 3.

As illustrated in FIGS. 4A and 4B, the ablation catheter 20 according to the present embodiment includes: a washing liquid supply channel 21 that is placed along the longitudinal direction at the central position in the radial direction of the catheter main body 6 and is opened on the leading end surface 6a; and a plurality of cooling liquid supply channels 22 that are placed along the longitudinal direction with intervals in the circumferential direction in the vicinity of the outer circumferential surface of the catheter main body 6 and are opened on the leading end surface 6a.

Figure 3:
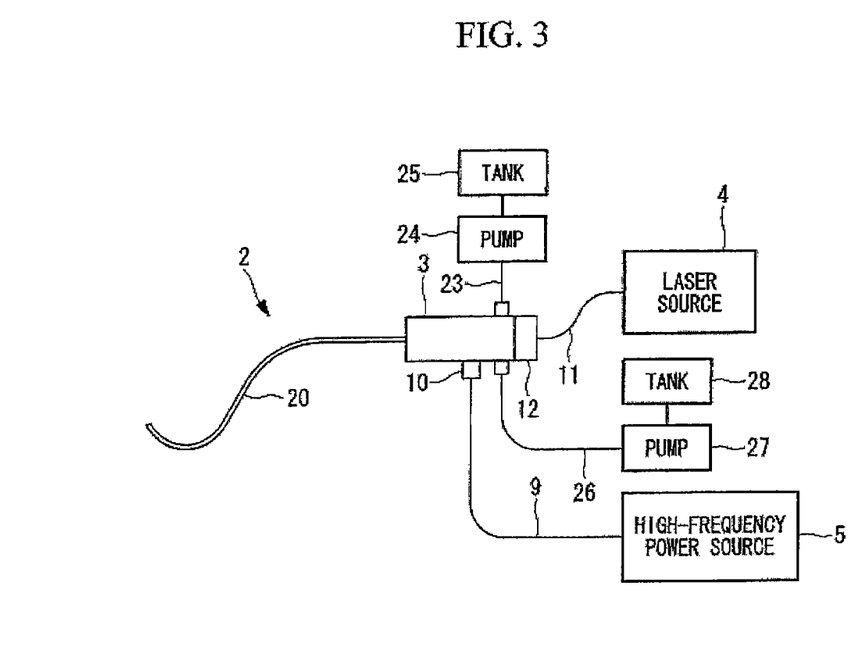
FIG. 3 is a diagram illustrating an ablation system to which an ablation catheter according to a second embodiment of the present invention is attached.

As illustrated in FIG. 3, the washing liquid supply channel 21 is connected to a tank 25 through a pipe 23 and a pump 24, and the cooling liquid supply channels 22 are connected to a tank 28 through a pipe 26 and a pump 27.

The tanks 25 and 28 each store, for example, transparent physiological saline as washing liquid or cooling liquid.

The pump 24 is actuated upon an actuation of the laser source 4 to supply the washing liquid stored in the tank 25 to the washing liquid supply channel 21 through the pipe 23, whereby the washing liquid is ejected from an opening 21a on the leading end surface 6a. Similarly, the pump 27 is actuated upon an actuation of the high-frequency power source 5 to supply the cooling liquid stored in the tank 28 to the cooling liquid supply channels 22 through the pipe 26, whereby the cooling liquid is ejected from openings 22a on the leading end surface 6a.

If the pump 24 is actuated and the washing liquid is thus ejected from the opening 21a on the leading end surface 6a, fine pieces of the adipose tissue or the cardiac muscle tissue evaporated by the application of the pulsed laser beam are washed away by the washing liquid, and the pulsed laser beam can be efficiently applied to the tissue.

That is, because the washing liquid supply channel 21, which is placed along the longitudinal direction of the catheter main body 6 and is opened on the leading end surface of the catheter main body 6, is provided, the washing liquid can be supplied to the leading end surface of the catheter main body 6 through the washing liquid supply channel 21. Consequently, the tissue fine pieces that exist between the emission ends of the optical fibers 8 and the adipose tissue or the cardiac muscle tissue and are evaporated from the tissue at the time of the laser beam application can be removed by the washing liquid, and the laser energy can be efficiently applied to the tissue.

Further, if the pump 27 is actuated and the cooling liquid is thus circulated in the cooling liquid supply channels 22, the electrode 7 wound around the outer surface of the leading end part of the catheter main body 6 is cooled by the cooling liquid. Hence, overheating of the electrode 7 due to feeding of a high-frequency current can be prevented, and the cardiac muscle tissue can be efficiently cauterized by the feeding of a high-frequency current, which is advantageous. That is, because the cooling liquid supply channels 22, which are placed along the longitudinal direction of the catheter main body 6 and circulate the cooling liquid in the vicinity of the electrode for ablation 7, are provided, the cooling liquid is circulated in the cooling liquid supply channels 22 at the time of feeding a high-frequency current by the electrode for ablation 7 and cauterizing the target tissue. Hence, overheating of the electrode for ablation 7 can be prevented, and a decrease in cauterization efficiency can be prevented.

Further, in the present embodiment, the leading ends of the optical fibers 8 are placed so as to be inclined inward or outward in the radial direction. This can enlarge the application range of the pulsed laser beam emitted from the emission ends 8a, and the adipose tissue or the cardiac muscle tissue in a range substantially equal to the outer diameter of the catheter main body 6 can be evaporated by the application of the pulsed laser beam. As a result, the catheter main body 6 can be easily moved toward the target site existing in the deep portion of the cardiac muscle tissue, which is advantageous.

Further, in such a configuration, the pulsed laser beam emitted from the leading end surface 6a of the catheter main body 6 diffuses with increasing distance from the leading end surface 6a, and the energy density thereof becomes lower accordingly. Hence, an effect of evaporating the adipose tissue or the like can be limited to only the vicinity of the leading end surface 6a, and the tissue removal can be prevented from occurring in a wide range.

Further, in the present embodiment, the washing liquid is ejected from the leading end surface 6a of the catheter main body 6 through the washing liquid supply channel 21, and the washing liquid supply channel 21 extends over the entire length in the longitudinal direction of the catheter main body 6. Hence, the washing liquid supply channel 21 may be used as an insertion hole of a guide wire at the time of introducing the ablation catheter 20 into the body.

Note that, in the present embodiment, the washing liquid is ejected from the opening 21a of the washing liquid supply channel 21 on the leading end surface 6a of the catheter main body 6, and the washing liquid is caused to flow between the emission ends 8a of the optical fibers 8 and the tissue. In this way, the tissue fine pieces existing in front of the emission ends 8a of the optical fibers 8 are washed, whereby the efficiency of the tissue removal by the pulsed laser beam emitted from the emission ends 8a of the optical fibers 8 is improved. In order to further improve this effect, as illustrated in FIG. 5, a baffle 29 that dams part of the flow of washing liquid A ejected from the opening 21a and causes the part to flow in the direction along the leading end surface 6a of the catheter main body 6 may be provided in front of the opening 21a of the washing liquid supply channel 21.

Figure 5:
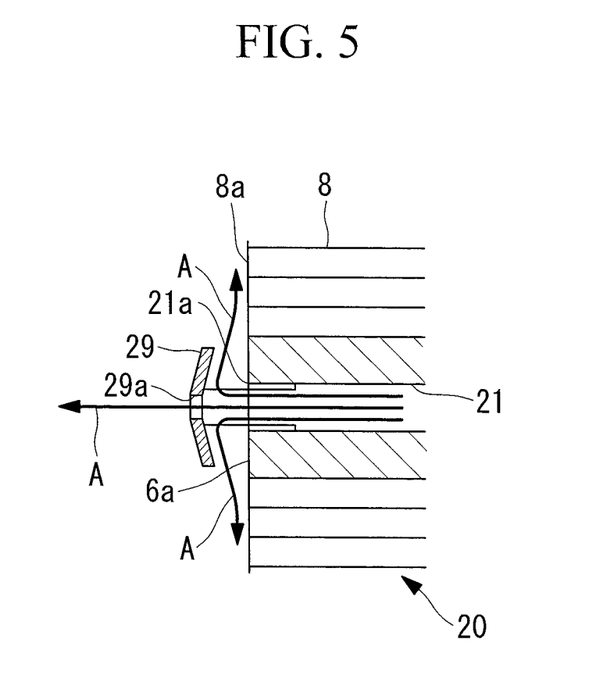
FIG. 5 is an enlarged longitudinal sectional view illustrating a modified example of the ablation catheter of FIGS. 4(A) and 4(B).

In the example illustrated in FIG. 5, the baffle 29 is made of a ring-like glass plate having a through-hole 29a in its center. The washing liquid A that passes through the through-hole 29a of the baffle 29 flows toward the tissue, and the washing liquid A dammed by the baffle 29 is caused to flow outward in the radial direction in the direction along the leading end surface 6a of the catheter main body 6. Accordingly, the tissue fine pieces that are evaporated and floating can be removed, and the tissue fine pieces are prevented from being attached to the emission ends 8a of the optical fibers 8. Further, because the baffle 29 is made of the transparent glass plate, the baffle 29 can be prevented from blocking the pulsed laser beam, and an effect of the tissue removal by the laser beam can be maintained.

That is, because the baffle, which is placed in front of the opening of the washing liquid supply channel and dams at least part of the supplied washing liquid to cause the part to flow in the direction along the leading end surface of the catheter main body 6, is provided, at least part of the washing liquid that is ejected frontward from the opening of the washing liquid supply channel hits against the baffle, and is caused to flow in the direction along the leading end surface of the catheter main body. As a result, the tissue fine pieces existing between the leading end surface and the tissue can be washed by the washing liquid, and can be prevented from being attached to the emission ends of the optical fibers.

Further, in the present embodiment, the washing liquid and the cooling liquid are respectively ejected from the opening 21a of the washing liquid supply channel 21 and the openings 22a of the cooling liquid supply channels 22 provided on the leading end surface 6a of the catheter main body 6. Alternatively, for example, a cooling liquid discharge channel, the illustration of which is omitted, may be provided instead of the washing liquid supply channel 21 in the center or together therewith. In such a manner, the cooling liquid ejected from the openings 22a of the cooling liquid supply channels 22 can be suctioned by the cooling liquid discharge channel to be discharged to the outside. The pump 24 connected to the washing liquid supply channel 21 may be reversed for suction at a negative pressure, whereby the washing liquid supply channel 21 may be used as the cooling liquid discharge channel.

In such a manner, for example, when a high-frequency current is fed to the electrode 7, which has been brought close to the target site by moving the ablation catheter 1 deeper inside of the cardiac muscle tissue while evaporating the cardiac muscle tissue with the pulsed laser beam, the pressure of the ejected cooling liquid can be prevented from driving the ablation catheter 1 out of the cardiac muscle tissue, and the electrode 7 can be stably positioned inside of the cardiac muscle tissue. Note that a washing liquid discharge channel may be provided instead of part of the cooling liquid supply channels 22, whereby the resistance caused by the washing liquid ejection during the movement of the ablation catheter 1 deeper inside of the cardiac muscle tissue may be reduced.

Next, an ablation catheter 30 according to a third embodiment of the present invention is described below with reference to the drawings.

In the following description of the present embodiment, elements having the same configurations as those in the ablation catheter 20 according to the second embodiment described above are denoted by the same reference signs, and description thereof is omitted.

Figure 7:
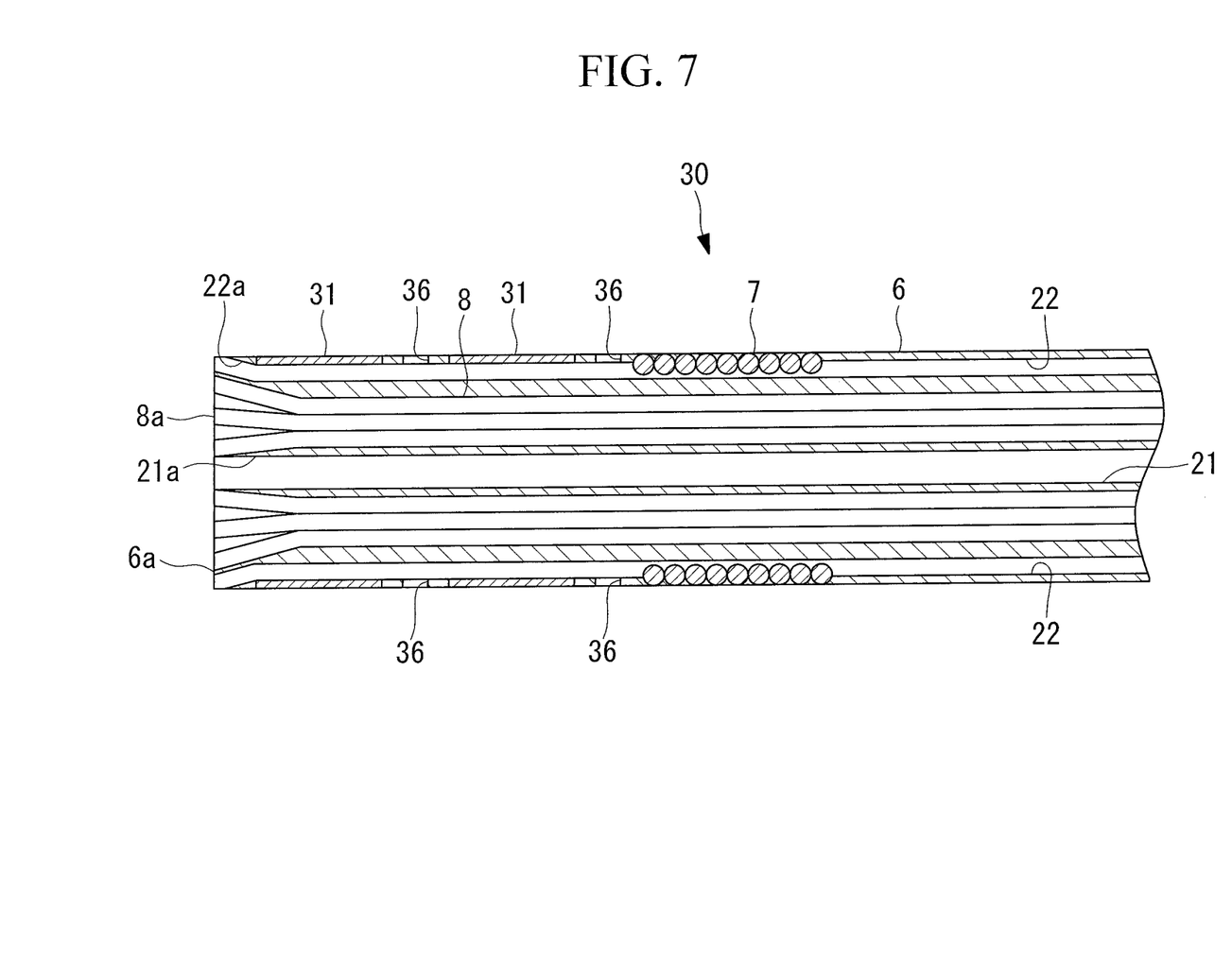
FIG. 7 is a longitudinal sectional view for describing a structure of a leading end part of the ablation catheter according to the present embodiment, the ablation catheter being used for the system of FIG. 6.

As illustrated in FIG. 7, an ablation catheter 30 according to the present embodiment includes paired electrodes for biopotential measurement 31 in the leading end part of the catheter main body 6.

Figure 6:
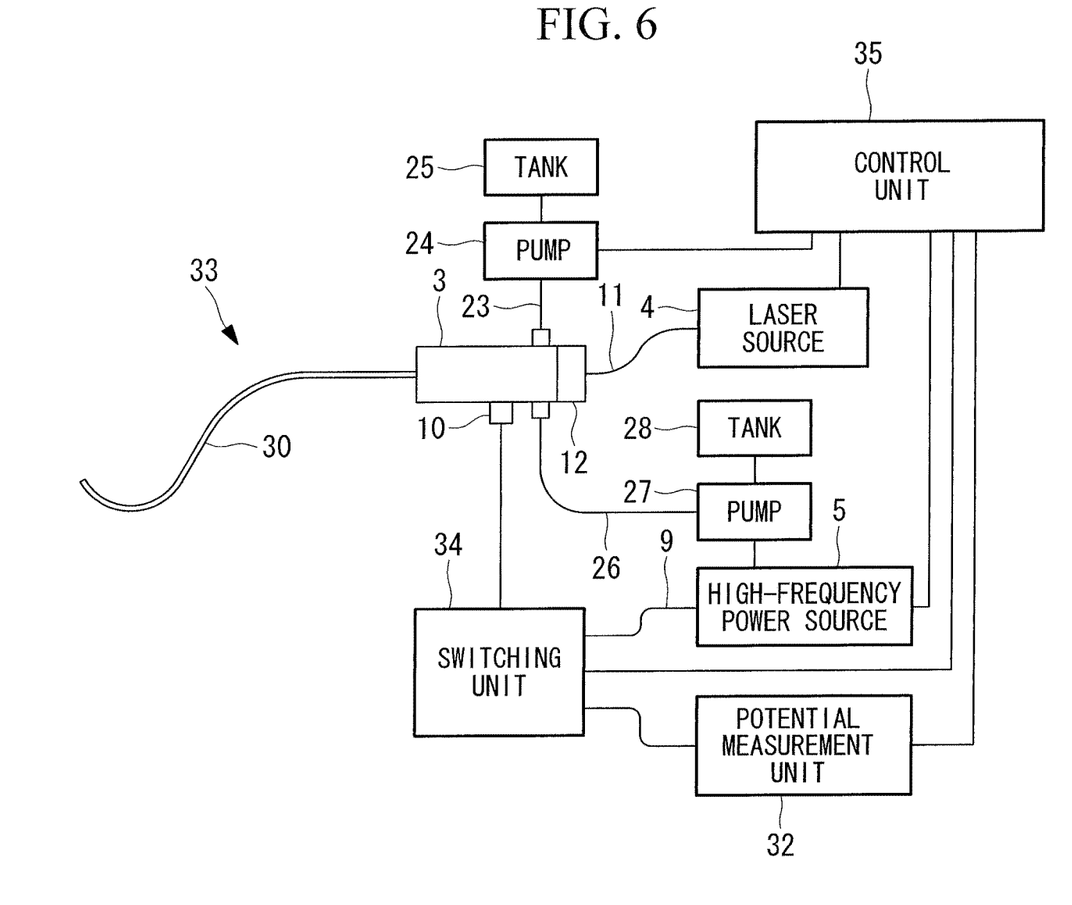
FIG. 6 is a diagram illustrating an ablation system to which an ablation catheter according to a third embodiment of the present invention is attached.

Moreover, an ablation system 33 illustrated in FIG. 6 includes a switching unit 34, and the switching unit 34 is connected to a control unit 35. At the time of feeding a high-frequency current, the control unit 35 orders the switching unit 34 to disconnect the paired electrodes for biopotential measurement 31 from a potential measurement unit 32 and short-circuit the paired electrodes 31 to the electrode for ablation 7. At the time of measuring a biopotential, the control unit 35 orders the switching unit 34 to disconnect the paired electrodes for biopotential measurement 31 from the electrode for ablation 7 and connect the paired electrodes 31 to the potential measurement unit 32.

Figure 9:
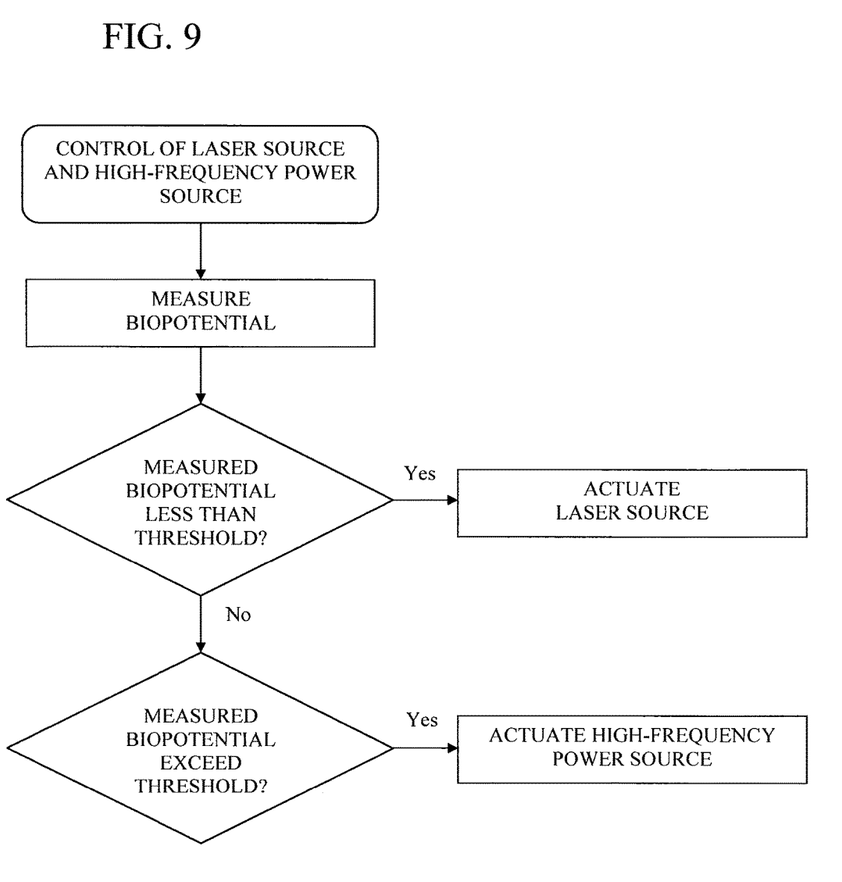
FIG. 9 is a flowchart showing a control of a laser source and a high-frequency power source on the basis of biopotential measured by a potential measurement unit.

Further, the control unit 35 may control the laser source 4 and the high-frequency power source 5 on the basis of the biopotential measured by the potential measurement unit 32, as shown in FIG. 9.

For a specific example, with the use of the fact that the biopotential measured by the potential measurement unit 32 is extremely small in a myocardial infarction portion, if the measured leading end potential is less than a predetermined threshold, it can be determined that the catheter leading end is located inside of the myocardial infarction portion or the adipose tissue and is not close to the target site existing in the deep portion of the cardiac muscle tissue. Hence, the adipose tissue or the cardiac muscle tissue is evaporated by actuating the laser source, and the catheter leading end is moved deeper inside of the tissue.

In contrast, if the biopotential exceeds the predetermined threshold and takes an abnormal value, it can be determined that the leading end part of the ablation catheter 30 is close to the target site. Hence, the cardiac muscle tissue is cauterized by actuating the high-frequency power source 5.

Note that, in FIG. 7, reference sign 36 denotes openings of the cooling liquid supply channels 22 that are formed on the outer surface of the catheter main body 6.

With the ablation catheter 30 thus configured according to the present embodiment, the switching unit 34 disconnects the paired electrodes for biopotential measurement 31 from the electrode for ablation 7, whereby the biopotential across the paired electrodes 31 can be measured by the potential measurement unit 32. Further, the switching unit 34 short-circuits the paired electrodes for biopotential measurement 31 to the electrode for ablation 7, whereby even the paired electrodes 31 can be used for ablation, thus achieving ablation in a wider region.

That is, with the ablation catheter 30 according to the present embodiment, when the leading end surface 6a of the catheter main body 6 is moved deeper inside of the cardiac muscle tissue, the intramyocardial potential, which is the biopotential across the paired electrodes 31, can be measured, so that it can be checked more reliably whether or not the leading end part of the catheter main body 6 has been inserted up to a diseased tissue (abnormal potential conduction portion) as the ablation target site inside of the cardiac muscle tissue.

That is, part of the electrode for ablation 7 placed in the leading end part of the catheter main body 6 is divided so as to be usable as the electrodes for biopotential measurement 31. Accordingly, the biopotential measurement from the tissue located in the leading end part of the catheter main body 6 is possible, and it can be checked whether or not the leading end part of the catheter main body 6 is close to the target position.

In the case where the potential measurement unit 32 determines that the leading end part of the catheter main body 6 has been inserted up to the target site, the control unit 35 actuates the switching unit 34 to short-circuit the paired electrodes to the electrode, and actuates the high-frequency power source to cauterize the cardiac muscle tissue by feeding a high-frequency current.

Figure 8:
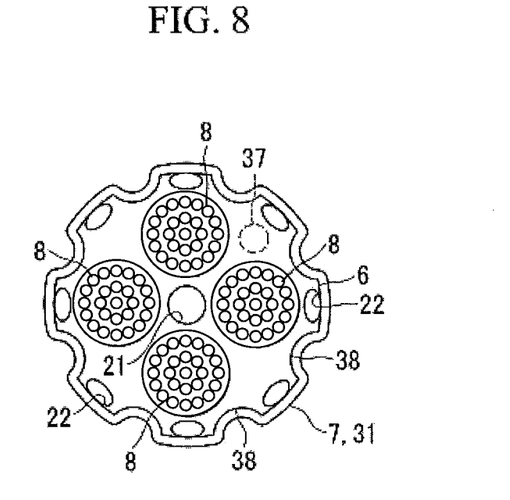
FIG. 8 is a front view illustrating a modified example of the ablation catheter according to the present invention.

Note that, in each embodiment described above, an optical fiber bundle obtained by bundling the plurality of optical fibers 8 is placed in a columnar pattern in the central portion of the catheter main body 6, or is placed in a circular pipe-like pattern around the washing liquid supply channel 21 in the center. Alternatively, as illustrated in FIG. 8, a plurality of bundles of the optical fibers 8 may be placed around the washing liquid supply channel 21 so as to be divided in the circumferential direction. In such a manner, for example, a position sensor 37 for detecting the leading end position of the ablation catheter 30 or a detectable member such as a magnetic material detectable from the outside of the body can be placed in a gap between the bundles of the optical fibers 8.

Further, as illustrated in FIG. 8, a plurality of grooves 38 may be provided with intervals in the circumferential direction on the outer circumferential surface of the catheter main body 6. If the grooves 38 are provided over the entire length in the longitudinal direction of the catheter main body 6, the grooves 38 can be used to discharge the cooling liquid and the washing liquid. Even during the discharge of the cooling liquid, the electrode 7 and the paired electrodes 31 can be cooled, and hence the cauterization efficiency can be further improved. The grooves 38 may be provided parallel to the longitudinal axis of the catheter main body 6, and may be provided in a spiral pattern.

Further, the baffle 29, which changes the flow direction so as to cause the washing liquid to flow outward in the radial direction along the leading end surface 6a of the catheter main body 6, is placed in front of the opening 21a of the washing liquid supply channel 21 in the center. Alternatively, the baffle 29 may be placed in front of the cooling liquid supply channels 22, and may cause the cooling liquid to flow inward in the radial direction along the leading end surface 6a of the catheter main body 6.

Further, physiological saline is given above as an example of the washing liquid and the cooling liquid. Alternatively, appropriate liquid, for example, a physiological electrolyte solution such as Ringer's solution, may be adopted as long as damage to a body tissue is small and washing and cooling functions can be fulfilled.

The following features are appended to a treatment method using an ablation catheter.

[Feature 1]

A treatment method for cauterizing a target site existing in a deep portion of a body tissue, comprising:

an insertion step of inserting a leading end part of an ablation catheter into a body cavity;

an opposition step of opposing the leading end part to the target site;

an emission step of emitting a pulsed laser beam from the leading end part to the body tissue; and a current feeding step of feeding a high-frequency current from an electrode in the leading end part to the target site.

[Feature 2]

The treatment method according to feature 1, further comprising a washing step of ejecting washing liquid from the leading end part to wash away an evaporated body tissue.

[Feature 3]

The treatment method according to feature 1, further comprising a cooling step of ejecting cooling liquid from the leading end part to cool the electrode.

[Feature 4]

The treatment method according to feature 2 or feature 3, further comprising a suction step of suctioning at least one of the washing liquid and the cooling liquid from the leading end part.

[Feature 5]

The treatment method according to any of feature 1 to feature 4, further comprising a measurement step of measuring a biopotential of the body tissue from the leading end part.

REFERENCE SIGNS LIST 1, 20, 30 ablation catheter
6 catheter main body 6a leading end surface
7 electrode (electrode for ablation)
8 optical fiber
8a emission end
21 washing liquid supply channel
22 cooling liquid supply channel
29 baffle
31 paired electrodes (electrodes for biopotential measurement)

What is claimed is:

1. An ablation catheter system comprising:
   an ablation catheter comprising:
      an elongated catheter main body;
      an optical fiber placed along a longitudinal direction of the catheter main body,
         wherein the optical fiber defines an emission end formed on a leading end surface of the catheter main body, and
         wherein the optical fiber is configured to guide a laser beam having high peak energy and to emit the laser beam guided therethrough from the emission end to ablate a first portion of a target;
      a cauterization electrode wound around a leading end part of the catheter main body,
         wherein the cauterization electrode feeds a high-frequency current to cauterize a second portion of the target; and
      a pair of biopotential measurement electrodes placed in the leading end part of the catheter main body,
         wherein the pair of biopotential measurement electrodes are configured to measure biopotential across the pair of biopotential measurement electrodes; and
   a controller configured to:
      control a laser source that generates the laser beam to control emission of the laser beam from the emission end of the optical fiber; and
      control a high-frequency power source that supplies the high-frequency current to control feeding of the high-frequency current through the cauterization electrode, based on the biopotential measured across the pair of biopotential measurement electrodes,
      wherein the controller is configured to control the laser source to generate the laser beam such that the laser beam is emitted from the emission end of the optical fiber in response to a first determination that the biopotential measured across the pair of biopotential measurement electrodes is less than a predetermined threshold, and
      wherein the controller is configured to control the high-frequency power source to supply the high-frequency current to the cauterization electrode in response to a second determination that the biopotential measured across the pair of biopotential measurement electrodes exceeds the predetermined threshold.

2. The ablation catheter system according to claim 1, wherein the ablation catheter further comprises a washing liquid supply channel placed along the longitudinal direction of the catheter main body, wherein the washing liquid supply channel defines an opening on the leading end surface of the catheter main body through which a washing liquid is supplied.

3. The ablation catheter system according to claim 2, wherein the ablation catheter further comprises a baffle placed in front of the opening of the washing liquid supply channel, wherein the baffle is configured to dam a part of washing liquid supplied through the opening of the washing liquid supply channel to cause the part to flow in a direction along the leading end surface of the catheter main body.

4. The ablation catheter system according to claim 1, wherein the ablation catheter further comprises a cooling liquid supply channel placed along the longitudinal direction of the catheter main body, wherein the cooling liquid supply channel is configured to cause cooling liquid to circulate in the vicinity of the cauterization electrode.

5. The ablation catheter system according to claim 1, wherein the laser beam guided through the optical fiber is a short pulsed laser beam for tissue evaporation.

* * * * *